United States Patent [19]

Reszka et al.

[11] Patent Number: 5,620,703
[45] Date of Patent: Apr. 15, 1997

[54] STIMULATING HEMATOPOIETIC ACTIVITY WITH CARBOPLATIN OR LOBAPLATIN

[75] Inventors: Regina Reszka, Schwanebeck; Iduna Fichtner, Berlin, both of Germany

[73] Assignee: Max-Delbrück-Centrum Fur Molekulare Medizin, Germany

[21] Appl. No.: 221,017

[22] Filed: Mar. 31, 1994

[30] Foreign Application Priority Data

Oct. 11, 1991 [DE] Germany ............... 41 34 158.9
Oct. 9, 1992 [WO] WIPO ............... PCT/DE92/00868

[51] Int. Cl.⁶ ............... A61K 9/127; A61K 31/28; A61K 31/56
[52] U.S. Cl. ............... 424/450; 424/810; 424/812; 514/171; 514/182; 514/885; 514/889; 514/908; 514/937; 514/938
[58] Field of Search ............... 514/171, 182, 514/885, 889, 908, 937, 938; 424/450, 810, 812, 153.1, 154.1

[56] References Cited

U.S. PATENT DOCUMENTS

| | | | |
|---|---|---|---|
| 4,372,949 | 2/1983 | Kodama et al. | 424/450 |
| 4,578,401 | 3/1986 | Keller et al. | |
| 4,673,567 | 6/1987 | Jizomoto | 424/450 |
| 4,710,457 | 12/1987 | DuPont et al. | 435/7 |
| 4,844,904 | 7/1989 | Hamaguchi et al. | 424/450 |
| 4,880,634 | 11/1989 | Speiser | 424/450 |
| 5,004,756 | 4/1991 | Ogawa et al. | 514/937 X |
| 5,021,234 | 6/1991 | Ehrenfeld | 424/450 X |
| 5,071,598 | 12/1991 | Baldeschwieler et al. | 424/450 X |
| 5,080,904 | 1/1992 | Iga et al. | 424/450 |
| 5,100,662 | 3/1992 | Bolcsak et al. | 424/450 X |
| 5,117,022 | 5/1992 | Khokhar et al. | |
| 5,230,900 | 7/1993 | Hakomori et al. | 424/450 |

FOREIGN PATENT DOCUMENTS 9102531  3/1991  WIPO.

OTHER PUBLICATIONS

R. Reszka et al., Preparation, Characterization, Therapeutic Efficacy, etc J. Microencapsulations 1987, vol. 4, No. 3, pp. 201–212.

Roman Perez–Solar et al., Clinical Development of Liposomal Platinum, J. Liposome Res., vol. 1, No. 4, 1990, pp. 437–449.

J. B. Bassett et al., Use of Temperature–Sensitive Liposomes, etc., Chem. Abstr., vol. 104, No. 18, p. 444, May 5, 1986, No. 155884f.

Primary Examiner—Richard D. Lovering
Attorney, Agent, or Firm—Schweitzer Cornman & Gross

[57] ABSTRACT

A process for stimulating hematopoietic activity in animals which comprises administering to a patient in need therefor a therapeutically effective amount of an agent containing as its active ingredient a water-soluble or lipid-soluble transition metal compound in a lyotropic mesophase, the agent optionally containing one or more additional carriers for stimulating hematopoietic activity.

6 Claims, No Drawings

STIMULATING HEMATOPOIETIC ACTIVITY WITH CARBOPLATIN OR LOBAPLATIN

This is a continuation-in-part of parent application PCT/DE92/00860, filed Oct. 9, 1992.

FIELD OF THE INVENTION

The present invention relates to the use of water-soluble or lipid-soluble transition metal compounds, pharmaceutical products, and methods for producing pharmaceutical products for antitumor therapy and/or to stimulate hematopoiesis for promoting blood formation, including leukocytes in animals. This makes the present invention particularly useful in the treatment of leukopenias, cancer and viral diseases which cause dramatic reduction or disturbances of leukocytes.

BACKGROUND OF THE INVENTION

Liposomes are closed, microscopic structures having concentrically arranged amphiphilic double layers which separate aqueous compartments from one another. Because of their similarity to cell membranes, liposomes have been investigated for many years as a multifunctional carriers and transporting systems for biologically-active substances, including prokaryotic and eukaryotic genes (D. Arndt, I. Fichtner (ed.): Liposomen Darstellung—Eigenschaften—Anwendung (The Preparation of Liposomes, Their Properties and Use), publ. Akademie-Verlag, Berlin (1986); G. Gregoriadis (ed.): Liposomes as drug carriers: Recent trends and progress, publ. John Wiley and Sons. Chichester (1988); G. Lopez-Berestein, I. J. Fidler (ed.): Liposomes in the therapy of infections diseases and cancer, publ. Alan R. Liss, N.Y., (1989); C. Nicolau, A. Gudd: Liposomes as carrier of DNA, Critical Rev. Therapeutic Drug Carrier Systems 6, 239–271 (1989)).

The work dealing with liposomal encapsulation of drugs is particularly extensive (I. Fichtner, D. Arndt: Stand und Perspektiven der Liposomenforschung (Status and Perspective of Liposome Research). Pharmazie 44, 752–757 (1989)). In comparison with other carrier systems (nano particles, artificial cells, etc.) liposomes offer various advantages, which can be utilized for such purposes as the encapsulation of cytostatic drugs, Examples of such advantages are:

the ability to select the composition, charge, size and stability, depending on the particular requirement, prevention of biological degradation of encapsulated substrates, the practically nonexisting immunological or toxic reactions, the frequently altered pharmacokinetics of the liposomal encapsulated substance, the altered distribution among the organs and the tropism to particular organs, the possibility of employing different targeting methods (lectins and antibodies.

Due to their amphiphilic character liposomes, can enclose water soluble as well as lipid soluble substances, almost all clinically established cytostatic, as well as some that are still in the development stage have been encapsulated and their physicochemical, biochemical and pharmacological properties have been characterized in comparison to the free compound (literature as above). When liposomally encapsulated antineoplastic drugs are used, a decrease in the toxicity is frequently observed, On the other hand, the therapeutic effectiveness of the liposomal and free form of the drug is approximately the same.

DESCRIPTION OF THE DRAWINGS

The invention is described below in detail, by reference being had to the drawing, wherein:

FIG. 1 shows the effect on leukocytes of carboplatin liposomes as a function of time and dosage;

FIGS. 2–3 show differential blood counts taken over several days;

FIG. 4 shows the effect of carboplatin liposomes with cyclophosphamide as a function of time and dosages; and FIG. 5 shows the effect on leukocytes of carboplatin liposomes in animals treated with zymosan, as a function of time and concentration.

DESCRIPTION OF THE INVENTION

It was observed that surprisingly the use of transition metal compounds in vesicular form, in addition to approximately the same or a significantly increased antitumor effectiveness, also/or leads to an above-average stimulation of the hematopoietic system.

In accordance with the invention, lipophilic transition metal compounds such as diethoxy-bis-(1-phenylbutane-1, 3-dionato)-titanium(IV) budotitane, trans-indazoliumbis-indazoletetrachlororuthenate (III) come into consideration for vesicular encapsulation. In addition to the lipophilic platinum derivatives, such as cis-[bis-(neodecanoatotrans-R,R)-1,2-diamino-cyclohexane platinum II (NDDP), cis-[(trans-1,2-cyclobutanedimethylamine)-(S)-2-oxidopropanoate platinum (II)] complex (lobaplatin), [1,1-cyclobutane dicarboxylate]-platinum (II) complex, CBDCA or carboplatin are platinum coordination compounds of the second generation, an analog of cisplatin, is also of special importance.

Accordingly, the process of the present invention for stimulating hematopoietic activity in animals such by stimulation of one or more of the leukocyte growth factors of interleukins, of α-interferon, and of tumor necrosis factor, comprises administering to a patient in need therefor a therapeutically effective amount of an agent containing as its active ingredient a water-soluble or lipid-soluble transition metal compound in a lyotropic mesophase, such as a micellar system, microemulsion, lamellar phase, and a hexagonal phase, the agent optionally containing one or more additional carriers, such as nano particles, for stimulating hematopoietic activity.

The transition metal is suitably platinum, titanium, or ruthenium and is suitably employed in vesicular form, suitably in a liposomal form obtained by treatment with a surfactant, or with a food emulsifier.

The therapeutic composition of the present invention comprises as active ingredient a therapeutically effective amount of the water-soluble, or lipid-soluble transition metal compound in the lyotropic mesophase, with the composition optionally containing one or more carriers. The composition suitably includes (i) a natural semi-synthetic or fully synthetic amphiphilic compound, such as liquid surfactant, or emulsifier; (ii) a steroid; (iii) a charged lipid component such as ethanolamine; (iv) the water soluble or lipid-soluble transition metal compound; and (v) a carrier, such as nano particles. Suitably the amphiphilic compound has the formula

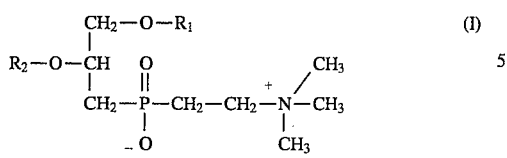

wherein $R_1$ and $R_2$ are independently of one another one or more of $C_{10-20}$ alkanoyl, alkenoyl, alkyl, and alkenyl residues, the steroid is R suitably of the formula

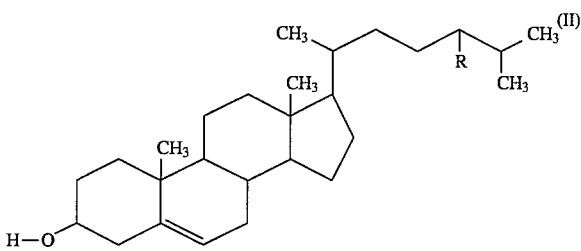

in which R is H when the steroid is cholesterol, and is $CH_2-CH_2-O-CH_2-CH_2-OH$ when the steroid is diethoxycholesterol, the charged lipid component is suitably the anion of dicetyl phosphate, palmitic acid or stearic acid, or of a phospholipid such as of phosphatidylserine or phosphatide acid, or of a sphingolipid, such as a sulfatide. The molar ratio of the amphiphilic steroid and charged lipid components is suitably from about 1:0.3 to about 1:1:0.5, and of the charged lipid and transitional metal suitably from about 2:1 to 10:1. The transition metal compound is suitably contained within a water phase, or lipid phase, or the lyotrophic mesophase, and over a lipophylic anchor to form a lyophilized product, and optionally resuspending the lyophilized product.

As used throughout the specification and the claims, the term "charged lipid component" means a component which has an initial charge, such as phosphatidylethanolamine, which charge is naturally pH dependent, being between 7.2 and 7.4. The charged lipid components are charged, whereas the amphiphilic compounds are usually not charged.

Carboplatin is 5 to 8 times more soluble in water than cisplatin, and due to its dicarboxylate group, has a higher stability in plasma, a longer half-life time in plasma, less irreversible binding to serum proteins and plasma proteins, and a more rapid glomerular excretion of the administered amount of platinum (K. D. Micerich, D. Barnes, L. C., Erickson: Cancer Res. 45, 4043–4047 (1985)).

Carboplatin is thus significantly less toxic to the kidneys than cis-DDP. However, it leads to a pronounced myelosuppression, which is dose limiting.

When carboplatin is encapsulated in liposomes of different composition, size, stability and charge and administered in equivalent doses (in comparison to the free substance) in the mouse model, (P 388), the therapeutic activity was reduced as shown in Table 1. However, a pronounced leukocytosis was observed at the same time. This above-average increase in the leukocyte count, achieved with the liposomal carboplatin, in combination with cyclophosphamide, led to the prevention of leukopenia, which limits the dosage of the substance as shown in FIG. 4. Testing the serum of treated animals with hematopoietic precursor cells (CFU-GM, CFU-G, CFU-M) in agar culture has shown that there is a greatly increased excretion of colony-stimulating factors, which can act synergistically with GM-CSF or IL-3 or themselves have CSF activity (IL-1 to IL-10, α-interferon, tumor necrosis factor, etc.). Since macrophages/monocytes are the natural targets of the liposomes, such cells can be shifted by encapsulation of transition metal compounds into an activated or tumoricidal state, a property, which can be exploited for the development of various pharmaceutical drugs. Accordingly, aside from the stimulation of hematopoiesis such as in the treatment of AIDS, it is also possible to employ combination chemotherapy for overcoming the dose limiting leukopenia of clinically established cytostatic drugs, and physiological production of colony-stimulating factors such as possible replacement of factors, which are produced by genetic engineering and are subject to considerable adverse reactions.

The results are next prodded that were obtained by using liposomal carboplatin pursuant to the present invention. The cytostatic was encapsulated phase evaporation vesicles in reverse (REV) were tested, since the amount of substance necessary for animal experiments can be encapsulated with the help of these liposomes. The vesicles are characterized by negative contrast electron microscopy with respect to their size and lamellarity and in selected cases with quasi-elastic light scattering for determining their size distribution. The encapsulation rate was determined indirectly by the colloidal bonding of platinum to tin chloride. The following results were obtained from repeated animal experiments involving P 388 leukemia of the mouse (i.p.); by measuring the results by the therapeutic index (% T/C) and by the toxicity parameters (body weight difference and leukocyte count) and were compared with results obtained from the control group comprised of animals treated with physiological salt solution after i.p. administration of 100 or 150 mg of carboplatin in free or liposomal form.

There were observed:

a decrease in the minor cytostatic effect of carboplatin on P 388 after liposomal encapsulation, and a significant increase in the leukocyte count after administration of the liposomal form of carboplatin, whereas the free form exhibited a leukopenic effect, as summarized in Table 1.

TABLE 1

Antineoplastic effectiveness of carboplatin liposomes as measured by P 388 leukemia (i.p.)
Administration i.p. Day 1

| Experiment Number | Gr. | Substance | mg/kg | T/C (%) | Tox./ Total | Body Weight Difference (%) | Leukocytes (G/l) |
|---|---|---|---|---|---|---|---|
| 3779 | A | Carboplatin | 100 | 128* | 0/8 | −1 | |
| | B | Carboplatin | 160 | 160* | 0/8 | −6 | |
| | C | Carboplatin liposomes | 100 | 100 | 0/8 | −3 | |
| | D | Carboplatin liposomes | 150 | 111 | 0/8 | −4 | |

TABLE 1-continued

Antineoplastic effectiveness of carboplatin liposomes as measured by P 388 leukemia (i.p.)
Administration i.p. Day 1

| Experiment Number | Gr. | Substance | mg/kg | T/C (%) | Tox./ Total | Body Weight Difference (%) | Leukocytes (G/l) |
|---|---|---|---|---|---|---|---|
| 3816 | A | Carboplatin | 100 | 122* | 0/8 | −1 | 2.7* |
| | B | Carboplatin | 150 | 122* | 0/8 | −8 | 2.2* |
| | C | Carboplatin liposomes | 100 | 100 | 0/8 | 0 | 9.4* |
| | D | Carboplatin liposomes | 150 | 100 | 0/8 | −1 | 8.1* |
| 3838 | F | Carboplatin | 100 | 133* | 0/10 | −1 | 2.7* |
| | G | Carboplatin | 150 | 133* | 0/10 | −5 | 1.8* |
| | D | Carboplatin liposomes | 100 | 111 | 1/10 | −12 | 26.4* |
| | E | Carboplatin liposomes | 150 | 111 | 1/10 | −12 | 19.1* |

*Significant (P < 0.05)

Carboplatin-containing REV, free carboplatin (100 mg/kg), empty REV and physiological salt solution were administered to tumor-free animals further to characterize the leukocyte effect, and blood samples were taken on various days. Leukocyte peaks occurred on the second day and on the seventh day with the liposomal encapsulated carboplatin. At 120,000 and 60,000 g/l, these peaks amounted to 10 and 5 times respectively of the normal value (FIG. 1).

Investigations of this leukocyte population in the differential blood count revealed a relative increase in the neutrophils and myelocytes on the first day, which indicated a shift to the left in the hematopoiesis (FIG. 2). On the seventh day, 50% lymphocytes and 45% neutrophils. could be detected, a trend which was still present on the sixteenth day (FIG. 3). The first peak indicates a release of leukocytes from the peripheral depots, while the second peak indicates a release of leukocytes from the bone marrow. This effect can be clinically utilized, for example, to decrease or to prevent the leukopenia of myelosupressive cytostatic drugs, as was confirmed by a combination with cyclophosphamide. Carboplatin liposomes (50 mg/kg) were administered one hour before 100 mg/kg of cyclophosphamide. Whereas cyclophosphamide, by itself, leads to a significantly pronounced leukopenia and carboplatin liposomes by themselves initiate leukocytosis, the combination causes normal leukocyte values to be reached (FIG. 4), as measured on the control group.

These results can be interpreted in the following way. The macrophages are the potential target of the liposomes. In order to test their effect, mice were treated with 100 mg/kg of the anticomplementary factor zymosan (a macrophage-blocking substance) s.c. or i.p. one day before the administration of the liposomes. Carboplatin liposomes, without pretreatment, showed the already described leukocyte stimulation. Administering zymosan s.c. first, before administering the liposomal, encapsulated preparation, did not interfere with this effect. After the zymosan was administered i.p., a distinct, even if incomplete, decrease in leukocyte stimulation could be deteaed (FIG. 5). It can be therefore assumed that the macrophages/monocytes, as natural target of the liposomes or of the cytokinins released by them (granulocytes-monocytes activation factors; interleukins, such as IL 3, IL 6) are primarily responsible for the hematopoietic effect. These findings are supported by first attempts to characterize the colony-stimulating activity in the bone marrow stem cell test. After i.p. administration of the liposomally encapsulated carboplatin, the serum of treated animals showed a 12-fold stimulation of colony growth. Liposomal carboplatin can thus become an endogenous stimulator of hematopoiesis. Consequently, improved effects can be expected in the combined use with radiation therapy or chemotherapy as well as in the treatment of AIDS.

Pursuant to the present invention, the use of liposomal lobaplatin also leads to a considerable increase in the leukocyte count. After an i.p. treatment, experiments with Lewis lung tumors (i.v.) showed a 3-fold increase from 9.2 to 33.4 G/l on the first day. The leukocyte count was conducted on the fourth day.

The invention is further described in the following illustrative examples.

EXAMPLE 1

A lipid film is produced from a mixture of 2328 mg of egg phosphatidyl choline, and 1132 mg of cholesterol (corresponding to USP XVIII), by the method of Singleton et al., J. Am. Oil Chemist's Soc. 42, 53–56 (1965). The film is dispersed with a mixture consisting of 450 ml of tetrahydrofuran and 60 ml of sterile, calcium-free, phosphate-buffered (pH 7.2–7.4) salt solution, which contains 900 mg of carboplatin. Subsequently, the organic solvent is distilled off in the rotary evaporator under different vacuums and the liposome dispersion, forming by way of an intermediate gel phase, is centrifuged for 1 hour at 40,000 rpm (3 times with, in each case, a 10-fold excess of buffer at 4° C.) to separate active ingredient that has not been encapsulated. After the pellet has been resuspended in the desired amount of buffer following the last centrifugation, the liposome solution is extruded over filter membranes (2.0; 1.0; 0.8; 0.4 and 0.2 μm). The vesicle suspension obtained can be stored at 4° C. and is suitable for parenteral (i.v.) administration.

EXAMPLE 2

Liposomes are prepared from a mixture of 2328 mg of hydrogenated egg phosphatidyl choline, and 1132 mg of-cholesterol (corresponding to USP XVIII), using the method of Reszka et al., Pharmazie 44, 503 (1989) in the same manner and with the additives and further treatment as described in Example 1. The resulting liposome dispersion is stored at 4° C. and is suitable for parenteral (i.v.) administration.

EXAMPLE 3

A lipid film is prepared of 11642 mg of hydrogenated egg phosphatidyl choline (prepared by the method of Reszka et al., Pharmazie 44, 503 (1989)), is dispersed in 225 ml of tetrahydrofuran and 30 ml of sterile, calcium-free, phosphate-buffered (pH 7.2 to 7.4) salt solution. The resulting suspension is treated further by the method described in Example 1. The resulting liposome dispersion is stored at 4° C. and is suitable for parenteral (i.v.) administration.

EXAMPLE 4

A lipid film, consisting of 150 mg of egg phosphatidyl choline (prepared by the method of Singleton et al., J. Am. Oil Chemist's Soc. 42, 53–56 (1965)), is dispersed in 3.86 ml of sterile, calcium-free, phosphate-buffered (pH 7.2–7.4) salt solution, which contains 19.35 mg of carboplatin. The resulting dispersion of multilayered liposomes is extrudable through filter membranes in the manner described. The liposome dispersion obtained is stored at 4° C. and is suitable for parenteral (i.v.) administration.

EXAMPLE 5

A lipid film of 150 mg of hydrogenated egg phosphatidyl choline (prepared by the method of Reszka et al., Pharmazie 44, 503 (1989)), is dispersed in 3.86 ml of sterile, calcium-free, phosphate-buffered (pH 7.2–7.4) salt solution, which contains 19.35 mg of carboplatin. The resulting dispersion of multilayered vesicles is further treated as described in Example 4 and is stored at 4° C. for parenteral (i.v.) administration.

EXAMPLE 6

A lipid film is prepared from a mixture of 129.2 mg of hydrogenated egg phosphatidyl choline (prepared by the method of Reszka et al., Pharmazie 44, 503 (1989)), 31.13 mg of cholesterol (corresponding to USP XVIII), and 9.04 mg of dicetyl phosphate (dihexadecyl hydrogen phosphate) of highest purity (Serva). The film was dispersed in a mixture consisting of 25 ml of tetrahydrofuran and 2.33 ml of sterile, calcium-free, phosphate-buffered (pH 7.2–7.4) salt solution, in which 50 mg of carboplatin were dissolved. The suspension is then further treated as described in Example 1. The resulting liposome dispersion is stored at 4° C., and is suitable for parenteral (i.v.) administration.

EXAMPLE 7

A lipid film is prepared from a mixture of 200 mg of egg phosphatidyl choline (prepared by the method of Singleton et al., J. Am. Oil Chemist's Soc. 42, 53–56 (1965)), 99.2 mg of cholesterol (corresponding to USP XVIII), 9.57 mg of stearylamine of highest purity (Serva) and 40 mg of budotitan. The resulting film is dispersed in a mixture of 15 ml of diethylether and 5 ml of sterile, calcium-free, physiological salt solution. The resulting suspension is further treated as described in Example 1. Since the budotitan can be completely encapsulated, separation by centrifugation is not required. The resulting liposome dispersion is stored at 4° C., and is suitable for parenteral (i.v.) administration.

EXAMPLE 8

A lipid film is prepared from 100 mg of egg phosphatidyl choline (prepared by the method of Singleton et al., J. Am. Oil Chemist's Soc. 42, 53–56 (1965)), and 5 mg of trans-indazoliumbisindazoletetrachlororuthenate (III). The resulting product is dispersed in 5 ml of sterile, calcium-free, physiological salt solution. The dispersion of multilayered liposomes is stored at 4° C., and is suitable for parenteral (i.v.) administration.

EXAMPLE 9

A lipid film is prepared from a mixture of 100 mg of hydrogenated egg phosphatidyl choline (prepared by the method of Reszka et al., Pharmazie 44, 503 (1989)), 49.51 mg of cholesterol (corresponding to USP XVIII), and 5 mg of trans-indazoliumbisindazoletetrachlororuthenate (III). The product is dispersed in 5 ml of sterile calcium-free, physiological salt solution. The resulting dispersion of multilayered liposomes is stored at 4° C., and is suitable for parenteral (i.v.) administration.

EXAMPLE 10

A lipid film is prepared from a mixture of 517 mg of hydrogenated egg phosphatidyl choline (prepared by the method of Reszka et al., Pharmazie 44, 503 (1989)), and 215 mg of cholesterol (corresponding to USP XVIII). The resulting product is dispersed in a mixture of 100 ml of tetrahydrofuran, and 13.3 ml of sterile calcium-free, phosphate-buffered (pH 7.2–7.4), sucrose-containing (338 mmoles/l) salt solution, which contains 200 mg of carboplatin. The dispersion is further treated as described in Example 1. The liposome dispersion is then lyophilized in a freeze drier, and is sealed under a protective gas. Before use, 13.3 ml of sterile, pyrogen-free distilled water are added to the dry preparation under sterile conditions, and the vessel is shaken for 10 minutes on a Vortex shaker. The resulting liposome dispersion is suitable for parenteral (i.v.) administration.

EXAMPLES 11–20

Are the same as Examples 1–10, with the exception that 900 mg of lobaplatin is used instead of carboplatin.

We claim:

1. A process for stimulating hematopoietic activity in animals which comprises administering to a patient in need therefor a therapeutically effective amount of an agent containing as its active ingredient carboplatin or lobaplatin in a lyotropic mesophase, which is one of more micellar system, microemulsion, lamellar phase, or a hexagonal phase, the agent optionally containing one or more additional carriers for stimulating hematopoietic activity.

2. The process of claim 1, wherein said optional additional carrier comprises nano particles.

3. The process of claim 1, wherein said hemapoetic activity is stimulated in a patient undergoing cytostatic therapy.

4. The process of claim 1, wherein said carboplatin or lobaplatin is employed in vesicular form obtained by treatment with a surfactant, or with a food emulsifier.

5. The process of claim 1, wherein said carboplatin or lobaplatin is in a liposomal form.

6. The process of claim 1, wherein said hematopoietic stimulation is the stimulation of one or more of the hematopoietic activation factors GM-CSF, G-CSF, M-CSF, IL-1 to IL-10, of α-interferon, and or tumor necrosis factor.

* * * * *

UNITED STATES PATENT AND TRADEMARK OFFICE
CERTIFICATE OF CORRECTION

PATENT NO. : 5,620,703
DATED : April 15, 1997
INVENTOR(S) : Regina Reszka et al.

It is certified that error appears in the above-identified patent and that said Letters Patent is hereby corrected as shown below:

Column 1, line 5 and 6 should read -- No. of PCT application is PCT/DE92/00868 --.

Signed and Sealed this

Twenty-second Day of July, 1997

Attest:

*Attesting Officer*

BRUCE LEHMAN

*Commissioner of Patents and Trademarks*